(12) United States Patent  
de Veer et al.

(10) Patent No.: US 8,797,534 B2
(45) Date of Patent: Aug. 5, 2014

(54) OPTICAL SYSTEM POLARIZER CALIBRATION

(71) Applicant: KLA-Tencor Corporation, Milpitas, CA (US)

(72) Inventors: Johannes D. de Veer, Menlo Park, CA (US); Leonid Poslavsky, Belmont, CA (US); G. Vera Zhuang, Santa Clara, CA (US); Shankar Krishnan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/034,869

(22) Filed: Sep. 24, 2013

(65) Prior Publication Data

US 2014/0043608 A1 Feb. 13, 2014

Related U.S. Application Data

(62) Division of application No. 13/164,130, filed on Jun. 20, 2011, now Pat. No. 8,570,514.

(51) Int. Cl.
*G01J 4/00* (2006.01)

(52) U.S. Cl.
USPC .......................................................... 356/366

(58) Field of Classification Search
USPC ................................................. 356/366, 369
See application file for complete search history.

(56) References Cited

U.S. PATENT DOCUMENTS

| | | | |
|---|---|---|---|
| 6,665,070 B1 * | 12/2003 | Yarussi et al. | 356/369 |
| 6,898,537 B1 | 5/2005 | McGahan | |
| 7,057,259 B2 * | 6/2006 | Arikado et al. | 257/618 |
| 7,115,818 B2 | 10/2006 | Kusano et al. | |
| 7,148,559 B2 * | 12/2006 | Chan et al. | 257/627 |
| 7,169,626 B2 * | 1/2007 | Chao et al. | 438/14 |
| 7,253,500 B2 * | 8/2007 | Iwase et al. | 257/618 |
| 7,277,182 B2 * | 10/2007 | Wegmann et al. | 356/494 |
| 7,449,374 B2 * | 11/2008 | Hierlemann et al. | 438/150 |
| 7,723,710 B2 * | 5/2010 | Campidell et al. | 250/559.44 |
| 7,786,551 B2 * | 8/2010 | Park et al. | 257/620 |
| 7,861,421 B2 * | 1/2011 | Kobayashi et al. | 33/1 N |
| 7,988,216 B2 * | 8/2011 | Ku et al. | 294/103.1 |
| 7,990,534 B2 * | 8/2011 | Li | 356/364 |
| 8,003,493 B2 * | 8/2011 | Ben Mohamed et al. | 438/458 |
| 8,158,489 B2 * | 4/2012 | Huang et al. | 438/455 |
| 2003/0067602 A1 | 4/2003 | Patel et al. | |
| 2003/0174328 A1 | 9/2003 | Russell et al. | |
| 2005/0146789 A1 * | 7/2005 | Wegmann et al. | 359/486 |
| 2008/0252888 A1 * | 10/2008 | Wegmann et al. | 356/365 |
| 2009/0319214 A1 | 12/2009 | Tian et al. | |
| 2011/0013175 A1 * | 1/2011 | Davis et al. | 356/72 |

* cited by examiner

*Primary Examiner* — Roy M Punnoose
(74) *Attorney, Agent, or Firm* — Luedeka Neely Group, P.C.; Rick Barnes

(57) ABSTRACT

An apparatus to calibrate a polarizer in a polarized optical system at any angle of incidence. The apparatus decouples the polarization effect of the system from the polarization effect of the sample. The apparatus includes a substrate with a polarizer disposed on the surface. An indicator on the substrate indicates the polarization orientation of the polarizer, which is in a predetermined orientation with respect to the substrate.

20 Claims, 4 Drawing Sheets

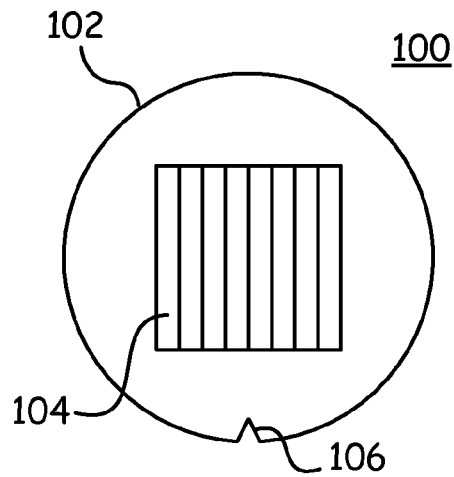
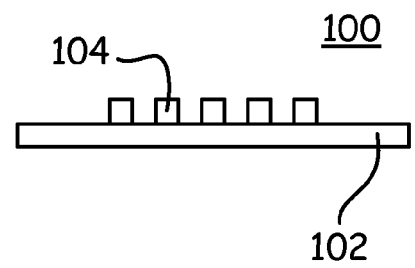
Fig. 1A   Fig. 1B
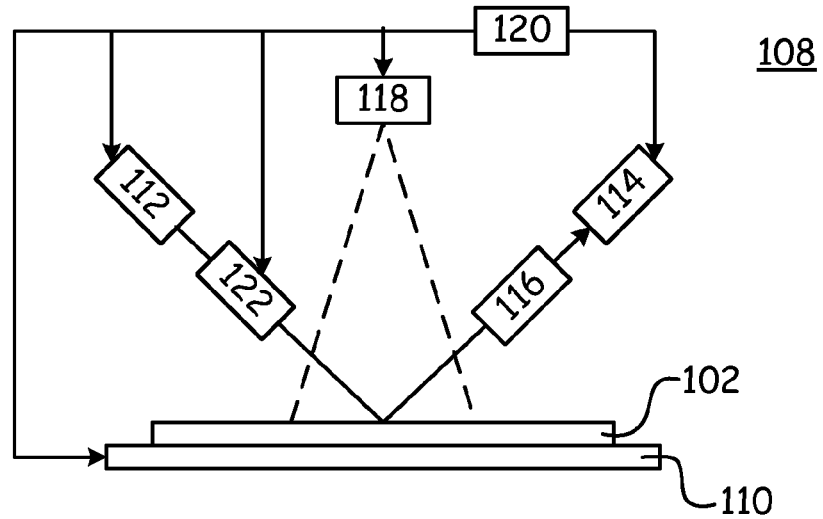
Fig. 1C

OPTICAL SYSTEM POLARIZER CALIBRATION

FIELD

This application claims rights and priority on prior pending U.S. patent application Ser. No. 13/164,130 filed 2011 Jun. 20. This invention relates to the field of optical metrology. More particularly, this invention relates to characterization, alignment, and calibration of a polarizer in an optical system, such as a spectral reflectometer.

INTRODUCTION

Currently, the calibration of the system polarizer in a polarized reflectometer uses the internal polarizer of the system in a transmission mode. Specifically, system polarization calibration is performed by stepping the internal polarizer of the system over a discrete set of angles while acquiring raw scans on a non-polarized reference sample (such as silicon oxide) at a fixed position. The acquired system-polarization response-curve on the non-polarizing reference sample, as a function of the internal polarizer stepping angle with respect to its home position and wavelength, is stored as a calibration curve for later characterization of polarized samples (such as grating samples).

In such methods, although the initial polarizer position is known at its home position of the stepper motor, its relative orientation with respect to a polarized sample is a system-fitting parameter that depends on the specific properties of the polarized sample, such as: the optical properties of the grating and films underneath it, period, critical dimension, profiles, and the orientation of the grating on the stage of the instrument. Such methods are generally limited to a broadband polarized reflectometer having a beam that is directed to the sample at an incident angle of zero degrees or less than ten degrees with respect to the perpendicular of the sample surface, in essence normal incidence or near normal incidence.

What is needed, therefore, is a more versatile polarization calibration method that decouples polarizing effects of the sample and the system polarization states, and can be used with an arbitrary angle of incidence.

SUMMARY

The above and other needs are met by a calibration apparatus with a substrate, a polarizer disposed on the substrate, and an indicator indicating a polarization orientation of the polarizer. In some embodiments the polarizer is a separate element that is attached to the surface of the substrate. In other embodiments the polarizer is a lithographic polarizer formed directly on the substrate.

DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 1A is a top plan view of a polarization calibration apparatus according to an embodiment of the present invention.

FIG. 1B is a cross-sectional side view of a polarization calibration apparatus according to an embodiment of the present invention.

FIG. 1C is a functional block diagram of a system to be calibrated using a polarization calibration apparatus according to an embodiment of the present invention.

DESCRIPTION

Figure 2A:
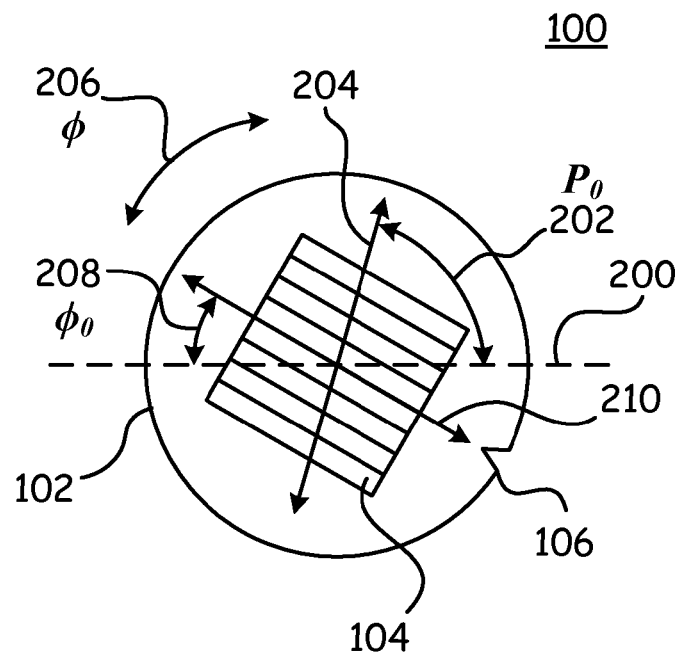
FIG. 2A is a combined top plan and logical view of a polarization calibration apparatus according to an embodiment of the present invention, depicting references and angles to be determined according to a first embodiment of the present invention.

With reference now to FIGS. 1A, 1B, and 1C, there is depicted a calibration apparatus 100 that is constructed by forming a polarizer 104 with a known polarization orientation and optical properties to a substrate 102, such as a standard silicon wafer. The polarizer 104 can work either in a transmission mode or in a reflection mode. The polarizer 104 is selected to have good optical qualities in regard to the polarized optical system 108 to be calibrated. These qualities include a high extinction ratio and low absorption over the spectral wavelength range of the system 108. The preferred operation is in reflection mode, in which the polarizer 104 is made of a metal grating structure on the substrate 102. The calibration apparatus 100 could be manufactured by patterning a lithographic polarizer 104 on a standard silicon wafer 102, or simply attaching a commercial polarizer 104 to a standard silicon wafer 102.

The calibration apparatus 100 is loaded onto the sample stage 110 of the system 108 in the same way as a polarized sample. With additional reference now to FIG. 2A, the notch 106 on the calibration apparatus 100 is used to establish the initial angle 208 $\phi_0$ between the orientation 210 of the calibration apparatus 100, relative to the reference frame 200 of the system 108 (such as the optical back plane or the plane of incidence). This angle 208 $\phi_0$ is further refined by using the built-in pattern recognition camera 118 that is often available in such systems 108, in combination with the coordinates of the stage 110 of the system 108. Once the angle 208 $\phi_0$ is accurately determined, a series of spectra $I(\phi, \phi_0, \lambda, P_0)$ are acquired from the calibration apparatus 100 by stepping stage 110 through angles 206 $\phi$ through a predetermined range of angles and at predetermined angle increments, while taking readings with the sensor 114. The complete set of data $I(\phi, \phi_0, \lambda, P_0)$ is reduced to $I(\phi', P_0)$, and plotted versus $(\phi'$, where $\phi' = \phi - \phi_0$ and $P_0$ is the angle 202 (between the system reference 200 and the internal polarizer 122 orientation 204) to be determined for the system 108. The polarizer orientation 202 $P_0$ of the system is extracted from the curve $I(\phi', P_0)$ by a nonlinear regression algorithm:

$$I(P_0, \phi') = A + B \cos 2(\phi' - P_0) + C \cos(4\phi' - 2P_0)$$

If the value of 202 $P_0$ falls outside of the specifications of the system 108, then the polarizer 122 in the system 108 can be adjusted using mechanical means until it meets the specification.

Figure 2B:
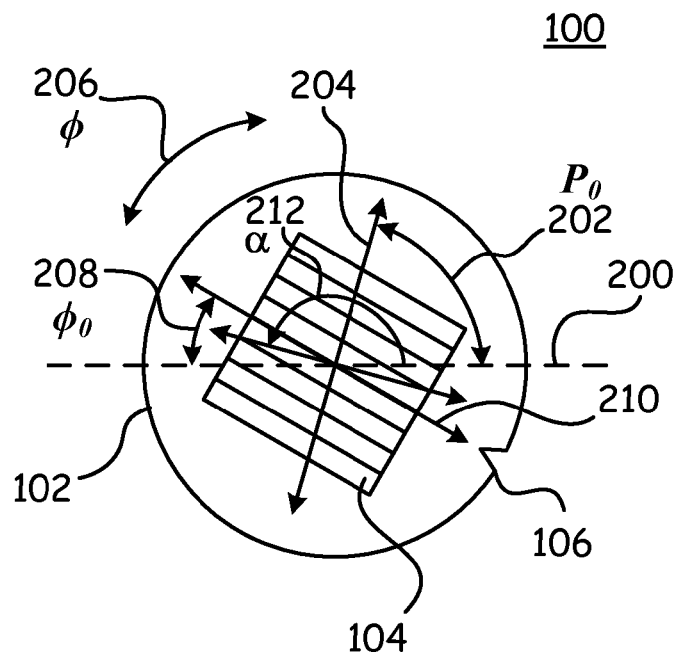
FIG. 2B is a combined top plan and logical view of a polarization calibration apparatus according to an embodiment of the present invention, depicting references and angles to be determined according to a second embodiment of the present invention.
Figure 4:
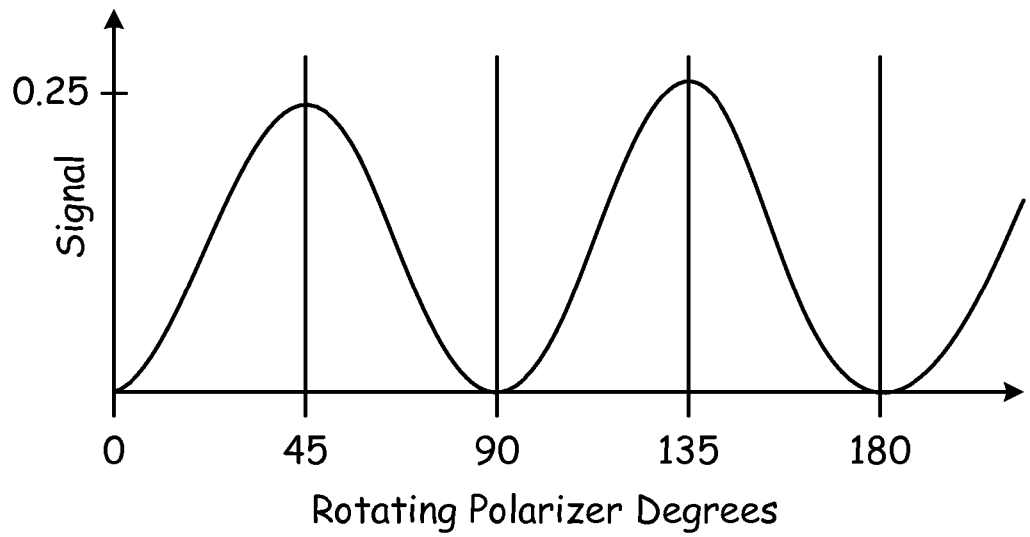
FIG. 4 is a chart of intensity as a function of rotating polarizer angle, with first polarizer at $P_0$ (0 degrees in the graph), and third, fixed polarizer at angle alpha (91 degrees in the graph), according to an embodiment of the present invention.

An alternate embodiment is depicted in FIG. 2B, in which a crossed analyzer 116 is inserted in the exit beam of the system 108, to improve the precision of the measurement of 202 $P_0$. The simulation depicted in FIG. 4 indicates that the resulting intensity curve is proportional to $\cos(4\phi'-P_0)$ when the fixed analyzer 116 is placed at about ninety degrees relative to 202 $P_0$. As a result, additional minimum 202 $P_0$ is introduced when the fixed analyzer is used with the calibration apparatus 100. The simulation depicted in FIG. 4 also reveals that if the analyzer 116 angle α 212 (between the system reference 200 and the analyzer 116 orientation) is off by as little as one degree (for example), the intensity curve contains a small $\cos(2\phi'-P_0)$ component. This component introduces about a six degree difference between the maxima, yet no change in the extinction angle 202 $P_0$. An additional advantage of using a fixed polarizer 122 during calibration is to allow for a more flexible orientation of the calibration apparatus 100 when there is a limited range of stage 110 rotation angles available.

Systems 108 often include polarizing elements other than a polarizer 122, such as a grating spectrometer. Those polarizing elements tend to introduce error into 202 $P_0$ if they are not properly accounted for. For example, the polarizer calibration angle 202 $P_0$ in a system 108 with only a polarizer 122 but without an analyzer 116 is susceptible to the alignment error of the grating spectrometer, since the spectrometer has a different spectral efficiency in regard to the p and s polarization states. To characterize the grating spectrometer misalignment angle φ, the internal polarizer 122 of the system 108 is removed and the polarization response curve is measured using the calibration apparatus 100. In this case, $$I(\phi_s,\phi')=A+B\cos 2(\phi'-\phi_s),$$

from which the angle $\phi_s$ can be extracted from the curve $I(\phi_s, \phi')$ using a nonlinear regression. This $\phi_s$ can be used to improve the accuracy of 202 $P_0$.

Figure 5:
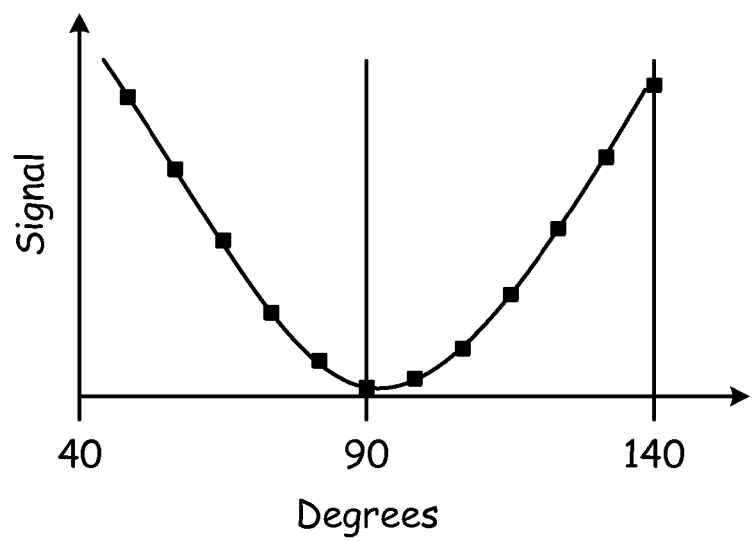
FIG. 5 is a calibration curve of a polarized optical system for signal versus rotation angle of a polarization calibration apparatus, according to an embodiment of the present invention.

FIG. 5 depicts the results from a polarizer calibration procedure using the calibration apparatus 100 and method as described. In this case, 202 $P_0$ is determined to be 89.84° relative to the optical reference frame 200 of the system 108. The discrete data points on the chart are integrated signals measured at angle 206 φ using the calibration apparatus 100.

Figure 3:
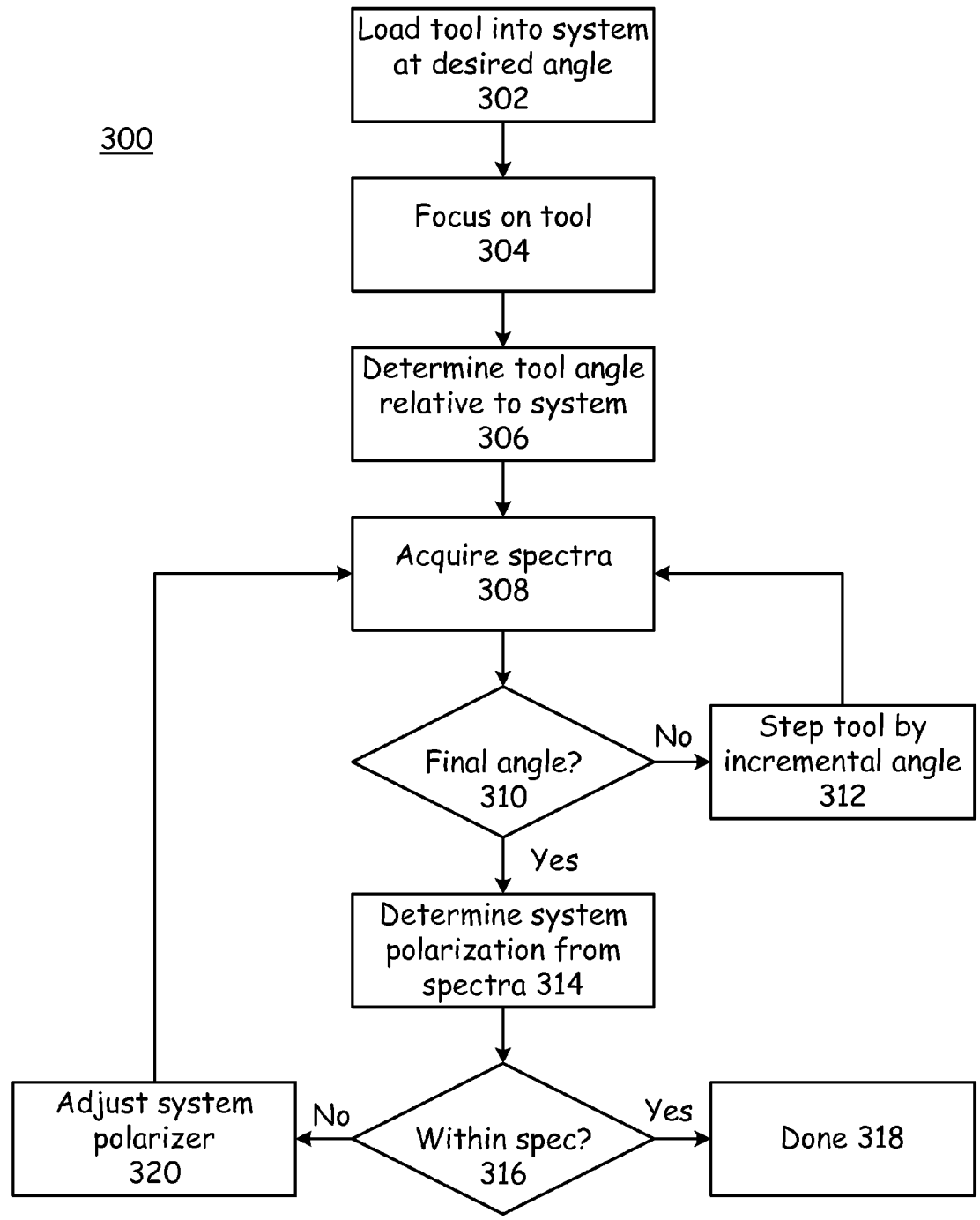
FIG. 3 is a flow chart of a method according to an embodiment of the present invention.

FIG. 3 depicts a flow chart of an embodiment of a method 300 according to the present invention. The apparatus 100 is loaded into the system 108, as given in block 302. The notch 106 is used to load the polarizer 104 at the desired position 210. The system 108 is then focused onto the apparatus 100 and otherwise initialed, as given in block 304. The initial apparatus angle 208 is then determined relative to the system reference 200. Spectra are then acquired at various angles with predetermine increments starting from that angle, using the sensor 114, as given in block 308. The method determines whether that reading is the final angle at which a spectrum is to be collected, as given in block 310. If it is not, then the apparatus 108 angle 206 is incremented according to a step, as given in block 312, and another spectrum is acquired, as given in block 308.

When all of the spectra have been acquired, then control flows from block 310 to block 314, and the angle 202 of system polarization 204 of internal polarizer 122 relative to the system reference 200 is determined, such as from the equations presented above, as given in block 314. If the angle 202 is within specification for the system 108, as determined in block 316, then the method concludes, as given in block 318. If not, then the system polarizer 122 is adjusted as needed, as given in block 320, and a new set of spectra are acquired, as described above, to verify the proper position of the polarizer 122.

The present polarization apparatus 100 and method can be used for calibrating the polarizer element 122 in a polarized reflectometer 108 at any arbitrary angle of incidence, including normal incident angle and any oblique incident angle. The method decouples the internal polarizer calibration from the spectrometer polarization effect. The method also establishes the initial position of the polarizer 122 using the system reference frame 200 (such as the plane of incidence), which is completely independent of the grating sample loading position. The method also characterizes the overall residual polarization of an unpolarized optical system 108.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An apparatus to calibrate a polarizer in a polarized optical system at any angle of incidence, by decoupling a polarization effect of the system from a polarization effect of a sample, the apparatus comprising a substrate having a polarizer disposed on a surface thereof, with an indicator on the substrate for indicating a polarization orientation of the polarizer, where the polarization orientation is in a predetermined orientation with respect to the substrate, and the polarizer configured to exhibit substantially complete extinction of system light in one orientation and substantially no absorption of system light in another orientation.

2. The apparatus of claim 1, wherein the apparatus is substantially transmissive to light from the system.

3. The apparatus of claim 1, wherein the apparatus is substantially reflective to light from the polarized optical system.

4. The apparatus of claim 1, wherein the polarizer is formed of a metal grating structure.

5. The apparatus of claim 1, wherein the substrate is a silicon substrate.

6. The apparatus of claim 1, wherein the indicator is a notch.

7. The apparatus of claim 1, wherein the polarizer covers only a portion of the surface of the substrate.

8. The apparatus of claim 1, wherein the polarizer is a separate structure that is affixed to the substrate.

9. The apparatus of claim 1, wherein the polarizer is integrally formed in the substrate.

10. The apparatus of claim 1, wherein the polarizer is formed of the same material as the substrate.

11. An apparatus to calibrate a polarizer in a polarized optical system at any angle of incidence, by decoupling a polarization effect of the system from a polarization effect of a sample, the apparatus comprising a polarizer formed by patterning a lithographic polarizer directly on a substrate surface, with an indicator on the substrate for indicating a polarization orientation of the polarizer, where the polarization orientation is in a predetermined orientation with respect to the substrate, and the polarizer configured to exhibit substantially complete extinction of system light in one orientation and substantially no absorption of system light in another orientation.

12. The apparatus of claim 11, wherein the apparatus is substantially transmissive to light from the system.

13. The apparatus of claim 11, wherein the apparatus is substantially reflective to light from the polarized optical system.

14. The apparatus of claim 11, wherein the polarizer is a grating structure formed in a metal layer on the substrate.

15. The apparatus of claim 11, wherein the substrate is a silicon substrate.

16. The apparatus of claim 11, wherein the substrate is a silicon oxide substrate.

17. The apparatus of claim 11, wherein the indicator is a notch.

18. The apparatus of claim 11, wherein the polarizer covers only a portion of the surface of the substrate.

19. The apparatus of claim 11, wherein the polarizer is formed of the same material as the substrate.

20. An apparatus to calibrate a polarizer in a polarized optical system at any angle of incidence, by decoupling a polarization effect of the system from a polarization effect of a sample, the apparatus comprising a polarizer disposed on a substrate surface, the polarizer formed of an etched grating layer formed in a metal layer on the substrate, with a notch in the edge of the substrate for indicating a polarization orientation of the polarizer, where the polarization orientation is in a predetermined orientation with respect to the substrate, and the polarizer configured to exhibit substantially complete extinction of system light in one orientation and substantially no absorption of system light in another orientation.

* * * * *